(12) United States Patent
Segawa et al.

(10) Patent No.: US 7,470,436 B2
(45) Date of Patent: Dec. 30, 2008

(54) WATER-SOLUBLE COMPOSITION CONTAINING COENZYME $Q_{10}$

(75) Inventors: Takeshi Segawa, Tokyo (JP); Atsuko Abe, Tokyo (JP); Tsuyoshi Minemura, Saitama (JP); Hironori Kubota, Tokyo (JP)

(73) Assignee: Nisshin Pharma Inc., Tokyo (JP)

( * ) Notice: Subject to any disclaimer, the term of this patent is extended or adjusted under 35 U.S.C. 154(b) by 371 days.

(21) Appl. No.: 10/537,433

(22) PCT Filed: Dec. 2, 2003

(86) PCT No.: PCT/JP03/15403

§ 371 (c)(1),
(2), (4) Date: Jun. 2, 2005

(87) PCT Pub. No.: WO2004/050072

PCT Pub. Date: Jun. 17, 2004

(65) Prior Publication Data

US 2006/0073176 A1  Apr. 6, 2006

(30) Foreign Application Priority Data

Dec. 4, 2002 (JP) ............................. 2002-352213

(51) Int. Cl.
*A61K 9/00* (2006.01)
*A61K 9/14* (2006.01)
*A61K 38/43* (2006.01)

(52) U.S. Cl. .............. 424/489; 424/400; 424/401; 424/439; 424/442; 424/94.1

(58) Field of Classification Search ........... 424/400, 424/401, 439, 442, 489
See application file for complete search history.

(56) References Cited

U.S. PATENT DOCUMENTS 6,303,662 B1 * 10/2001 Nagahama et al. .......... 424/522

FOREIGN PATENT DOCUMENTS

| JP | 361012632 A | * | 1/1986 |
| JP | 2000-212066 | | 8/2000 |
| JP | 2002-193740 | | 7/2002 |
| WO | WO 01/12229 | | 2/2001 |

* cited by examiner

*Primary Examiner*—Johann R. Richter
*Assistant Examiner*—Konata M George
(74) *Attorney, Agent, or Firm*—Antonelli, Terry, Stout & Kraus, LLP.

(57) ABSTRACT

A water-soluble composition comprising (A) coenzyme $Q_{10}$ of 5-40% by weight, (B) monoester of polyglycerol with average polymerization degree of 10 and fatty acid with 18 carbon atoms of 5-30% by weight, (C) mono-, di-, tri- or penta-ester of polyglycerol with average polymerization degree of 3-6 and fatty acid with 18 carbon atoms of 1-18% by weight, and (D) water, wherein its average particle diameter is 110 nm or smaller. It is superior in acid resistance, salt-resistance and heat resistance, and further enables to maintain the good water-soluble state being blended to medicines, foods and beverages, cosmetics, feeds, additives usually employed therein.

18 Claims, 2 Drawing Sheets

WATER-SOLUBLE COMPOSITION CONTAINING COENZYME $Q_{10}$

TECHNICAL FIELD

The present invention relates to a water-soluble composition containing coenzyme $Q_{10}$. The invention further relates to a process for producing the water-soluble composition, medicines, foods and beverages, cosmetics and feeds containing the water-soluble composition. Specifically, the invention relates to water-soluble composition capable of containing coenzyme $Q_{10}$ with high concentration, superior in storage stability such that coenzyme $Q_{10}$ will not precipitate, deposit or float during a long term preservation, and also superior in absorbency such that it gives absorbency even under fasting. Furthermore, the invention relates to medicines, foods and beverages, cosmetics and feeds comprising composition containing coenzyme $Q_{10}$ superior in heat resistance, acid resistance and salt-resistance that are required for the application.

BACKGROUND ART

Coenzyme $Q_{10}$ corresponds to ubiquinones (formula: $C_{59}H_{90}O_4$; molecular weight: 863.4) that is 2,3-dimethoxy-5-methyl-6-polyprenyl-1,4-benzoquinone with a side-chain comprising 10 isoprene units, and existing in higher animal. It is one kind of coenzyme Q known as ubidecarenone or coenzyme $Q_{10}$. The physical property of coenzyme $Q_{10}$ is known as orange crystal, which is a fat-soluble substance having melting point at about 49° C. Coenzyme $Q_{10}$ is known as not only a coenzyme having biological activity but also a vitamin-like active substance having function of improving oxygen utilization efficiency. Coenzyme $Q_{10}$ is considered to be essential in production of adenosine triphosphate in mitochondria, and it is reported to be effective for the treatment of cardiac disease, hypertension, rheumatic valve affection or inflammation of alveolar each by improving its immune function. It is also employed for the treatment of congestive heart failure or cerebrovascular disorder, for prevention of adverse effects of anticancer agents (prevention of cardiopathy by adriamycin), for fatigue reactivation, for energy activation, and for antioxidation of in vivo active oxygen. Its validity to prevent from aging employed as skin external preparation is expected, too. Thus, coenzyme $Q_{10}$ has high bioactivity and it is believed as highly safe substance existing in vivo.

In late years, various kinds of technology are disclosed regarding coenzyme $Q_{10}$ under such situations.

For example, JP-A-60-199814 discloses a fatty emulsion obtained by processing nonionic surfactant such as polyethylene glycol, hardened castor oil polyoxyethylene-(20)-ether and so on with Manton Gaulin type high pressure homogenizer (500 to 550 kg/cm$^2$).

JP-A-63-150221 discloses an emulsified composition for pharmaceutical medicines with excellent absorbency obtained by employing ubiquinone as crystalline agent, dissolving it into adipic acid or an oil such as soybean oil and so on in supersaturated condition, preparing O/W type microemulsion with the use of surfactant such as polyoxyalkylene base, polyglycerol fatty acid ester, Tween base or so, and by adding another O/W type microemulsion.

EP-494651B1 and U.S. Pat. No. 5,298,246 disclose a composition with improved absorbency prepared by dissolving ubiquinone into oil, emulsifying with the use of a fat globule membrane in mammals milk, and by fractionating particles of specified particle diameter (1-5 μm).

JP-A-2000-212066 discloses aqueous emulsion containing fat-soluble substance prepared by combining ubiquinone as lipid-soluble substance, polyglycerol fatty acid ester as emulsifier and glycerol-phosphoric lipid, further adding polyalcohol and water, and then stirring, followed by homogenization processes with high pressure of 500-2000 kg/cm$^2$.

Coenzyme $Q_{10}$ fat emulsion described in JP-A-60-199814 has problems that its particle size is large and that it is inferior in transparency.

The composition disclosed in EP-494651B1 and U.S. Pat. No. 5,298,246 wherein coenzyme $Q_{10}$ is necessarily dissolved in oil has problems that its particle diameter is large and that it is inferior in transparency. Besides, there is problem that it is inferior in heat resistance, acid resistance and salt-resistance each needed for manufacturing foods and beverages.

JP-A-63-150221 further teaches cosmetic liquid that is superior in storage stability under low temperature, however in this technology, transparency becomes poor and precipitation occurs along with decrease of the liquid temperature, and there is problem that it is inferior in heat resistance, acid resistance and salt-resistance each needed for manufacturing foods and beverages.

JP-A-2000-212066 also teaches oil-in-water type microemulsion applicable to various kinds of oily substances. However, this technology has problems of being inferior in acid resistance, salt-resistance and heat resistance under various conditions.

JP-A-9-168369 discloses a solubilized oil and fat composition containing polyglycerol fatty-acid ester, water and food additives. However, the composition has problems of being inferior in transparency and stability.

A water-soluble composition containing coenzyme $Q_{10}$ is expected to satisfy the following requirements:

(1) small particle sizes, and superior in transparency;
(2) high concentration of coenzyme $Q_{10}$ without needing oil components for dissolving or dispersing;
(3) superior in a feeling of delicious dining and taste;
(4) without needing special conditions or complicated processes in manufacturing; and
(5) superior acid-proof heat resistance and salt-tolerant heat resistance which are necessary for addition into various food.

However, formulation of coenzyme $Q_{10}$ by emulsification is generally accompanied by difficulty because coenzyme $Q_{10}$ is insoluble in water, instable against light, heat or alkali, and high crystallinity. Further, even once after preparing emulsion, the problem that separation, deposition, precipitation or floating will occurs by the re-crystallization of coenzyme $Q_{10}$. Although the concentration of coenzyme $Q_{10}$ in water-soluble compositon is needed to increase to get sufficient effect of coenzyme $Q_{10}$, it is difficult to aqueously solubilize because of its dissolution retardancy and high crystallinity.

Moreover, a solubilized solution without requiring an ordinary oily component in an occasion of adding coenzyme $Q_{10}$ in foods and beverages, cosmetics or so; superior in transparency, acid resistance, salt-resistance and heat resistance that are altogether necessary when blending with the foods and beverages, cosmetics or so; excellent in emulsion stability and storage stability; further capable of containing coenzyme $Q_{10}$ with high concentration was eagerly demanded. Still further, improving absorbency of coenzyme $Q_{10}$ was also demanded because the in vivo absorbency was poor.

Accordingly, the present invention has an object of overcoming the above problems and providing a water-soluble composition containing coenzyme $Q_{10}$ and a process for producing thereof without employing solvent such as oils, superior in storage stability such that coenzyme $Q_{10}$ will not precipitate, deposit or float during a long term preservation, also superior in texture, taste, acid resistance, salt-resistance, heat resistance in an occasion of addition into medicines, foods and beverages, cosmetics and feeds; and further improving bioabsorbency conspicuously. Another object of the invention is to provide medicines, foods and beverages, cosmetics and feeds together with their administration superior in transparency even after blending the composition into them without deposition, precipitation, or floating of coenzyme $Q_{10}$.

DISCLOSURE OF THE INVENTION

As the result of intensive researches and studies to achieve the above object by the present inventors, it was found that forming oil-in-water type emulsion with the use of two kinds of specific surfactant will keep excellent solubilized states of coenzyme $Q_{10}$ in high concentration and will improve bioabsorbency, resulting in completion of the invention.

Namely, the invention provides the following [1] to [8]:

[1] A water-soluble composition comprising (A) coenzyme $Q_{10}$ of 5-40% by weight, (B) monoester of polyglycerol with average polymerization degree of 10 and fatty acid with 18 carbon atoms of 5-30% by weight, (C) mono-, di-, tri- or penta-ester of polyglycerol with average polymerization degree of 3-6 and fatty acid with 18 carbon atoms of 1-18% by weight, and (D) water, where its averaged particle diameter is 110 nm or smaller;

[2] The water-soluble composition of item [1], wherein the fatty acid composing component (B) is stearic acid, oleic acid or linoleic acid, and wherein the fatty acid composing component (C) is stearic acid, oleic acid or linoleic acid;

[3] The water-soluble composition of item [1] or [2], further comprising (E) solubilizer of 10-80% by weight.

[4] The water-soluble composition of item [3], wherein the solubilizer is gums, saccharides or polyhydric alcohol;

[5] The water-soluble composition of item [1], wherein a weight ratio of [(A)]/[(B)+(C)] is within the range of 1/(5-0.7) and wherein a weight ratio of [(B)]/[(C)] is within the range of 1/(0.2-1);

[6] A process for producing the water-soluble composition according to item [1] which comprises the steps of:

(I) heating and dissolving components (B), (C), (D) and optionally the component (E);

(II) adding component (A) and mixing; and at least one selected from (III) homogenizing the resultant mixture with a shear force of 750 m/minute or greater as a peripheral-speed of an agitation blade using a homo-mixer; or (IV) homogenizing the resultant mixture under a homogenizing pressure of 98 MPa (1,000 kg/cm$^2$) or greater using a homogenizer.

[7] The process of item [6], wherein the step (III) or (IV) is repeated, or wherein the steps (III) and (IV) are successively carried out.

[8] Medicines, foods and beverages, cosmetics and feeds containing the water-soluble composition of item [1].

THE PREFERRED EMBODIMENT TO CARRY OUT THE INVENTION

Figure 1:
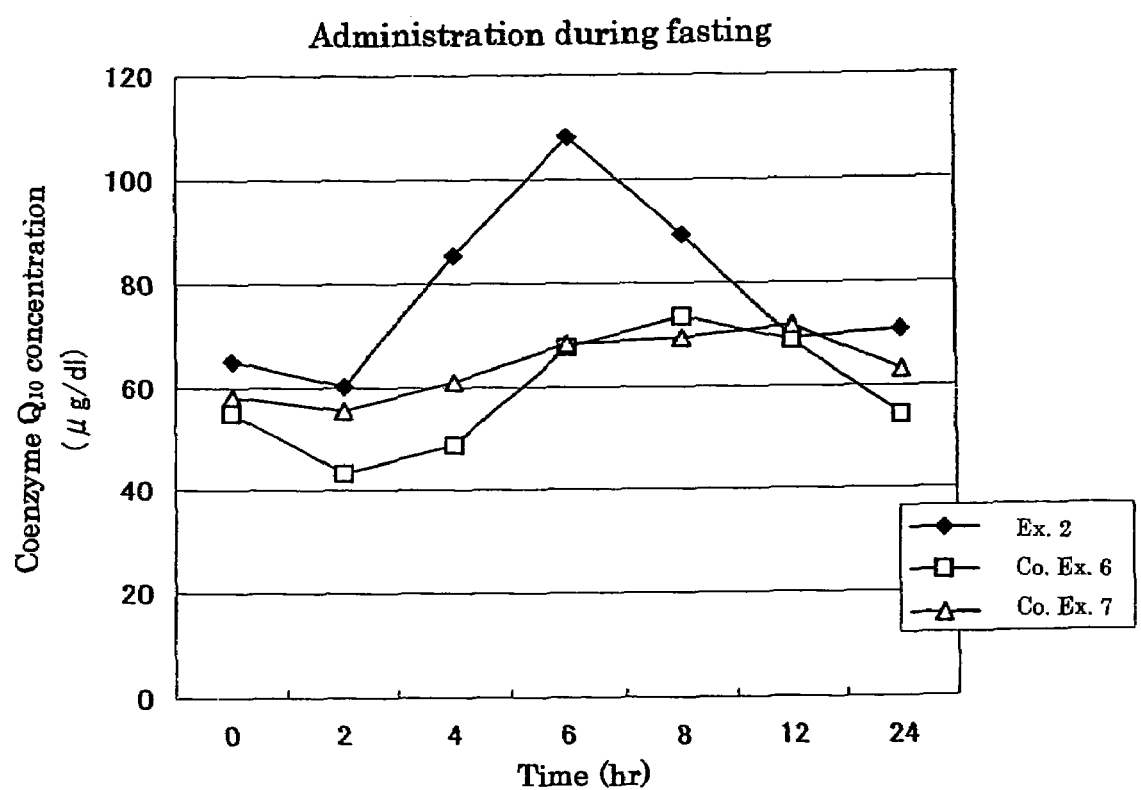
FIG. 1 is a graph which illustrating the absorbency of coenzyme $Q_{10}$ in fasting intake.

The present invention relates to a water-soluble composition which comprises (A) coenzyme $Q_{10}$ of 5-40% by weight, (B) monoester of polyglycerol with average polymerization degree of 10 and fatty acid with 18 carbon atoms of 5-30% by weight, (C) mono-, di-, tri- or penta-ester of polyglycerol with average polymerization degree of 3-6 and fatty acid with 18 carbon atoms of 1-18% by weight, (D) water, and optionally (E) solubilizer of 10-80% by weight, wherein averaged particle diameter is 110 nm or smaller, preferably 80 nm or smaller, and more preferably 60 nm or smaller.

Component (A)

Coenzyme $Q_{10}$ as the component (A) is described as ubiquinone 10, ubidecarenone or coenzyme $UQ_{10}$ in Japanese pharmacopoeia. Coenzyme $Q_{10}$ employed in the present invention may be extracted from the heart of animals such as cattle or so, and it may be prepared through a synthetic method or a fermentation method. Specific examples of the commercially available coenzyme $Q_{10}$ include food material coenzyme $Q_{10}$ (Nissin Pharma Inc.), Kaneka coenzyme $Q_{10}$ (Kaneka Corporation), CoEnzyme $Q_{10}$ (Asahi Kasei Corporation), etc. Although a purity of coenzyme $Q_{10}$ is not particularly specified depending on the application, impurity and its contents, or quality of the products must be sufficiently under control depending on the utilization because the water-soluble composition of the present invention is applied to medicines, beverages and foods including various supplements or so, and cosmetics.

An amount of coenzyme $Q_{10}$ in the composition is within the range of 5-40% by weight, preferably 7-30% by weight, and more preferably 9-25% by weight.

When the amount of coenzyme $Q_{10}$ is smaller than 5% by weight, it is not favorable because the quantity of the water-soluble composition will increase in order that the aimed effect is achieved. When the content of coenzyme $Q_{10}$ exceeds 40% by weight, it is also unfavorable because maintaining solubilized states of coenzyme $Q_{10}$ in the composition will become difficult.

Component (B)

An amount of component (B), i.e., monoester of polyglycerol with average polymerization degree of 10 and fatty acid with 18 carbon atoms is within the range of 5-30% by weight. Preferably the amount may be within the range of 5-25% by weight, more preferably within the range of 7-20% by weight from the viewpoint of emulsion stability or flavor.

The fatty acid composing component (B) is not particularly limited as far as the fatty acid has 18 carbon atoms, preferably stearic acid, oleic acid, linoleic acid or so may be employed. Accordingly, decaglycerinmonostearate, decaglycerimonooleate, decaglycerinmonolinoleate or so is preferable as the monoester of component (B), but not limited thereto. Further, any mixture of the above monoesters may be employable.

Such a monoester of polyglycerol and C18 fatty acid is commercially available, and the examples include Sunsoft Q-18S, Sunsoft Q-17S (Taiyo Kagaku Co., Ltd.), Poem J-0381 (Riken Vitamin Co., Ltd.), SY-Glyster MO-750, FRL-1 (Sakamoto Yakuhin Kogyo Co., Ltd.), O-15 D (Mitsubishi-Kagaku Foods Cooperation).

The purity of the monoester is not particularly limited, and it may include a certain amount of di-ester and tri-ester besides polyglycerol fatty acid monoester with average polymerization degree of 10 considering the production thereof.

Component (C)

An amount of component (C), i.e., polyglycerol with average polymerization degree of 3-6 and mono-, di-, tri- or penta-ester with 18 carbon atoms is within the range of 1-18% by weight, preferably 2-18% by weight, more preferably 3-9% by weight from the viewpoint of emulsion stability or flavor.

The fatty acid composing component (C) is not particularly limited as far as the fatty acid has 18 carbon atoms, preferably stearic acid, oleic acid, linoleic acid or so may be employed.

Examples of polyglycerol ester with average polymerization degree of 3-6 include mono-, di-, tri- and penta-ester of C18 fatty acid and triglycerin, tetraglycerin, pentaglycerin, or hexaglycerin. Particularly preferable example is pentaglycerin monoester.

The glycerin part is polyglycerol with average polymerization degree of 3-6, and a mixture thereof is also employable.

Examples of mono-, di-, tri- or penta-ester of polyglycerol and fatty acid composing component (C) include mono-, di-, tri- or penta-stearate of tri-, tetra-, penta- or hexa-glycerin; mono-, di-, tri- or penta-oleate of tri-, tetra-, penta- or hexa-glycerin; mono-, di-, tri- or penta-linoleate of tri-, ztetra-, penta- or hexa-glycerin; and these mixture may be also employable.

Such esters of polyglycerol and C18 fatty acid are commercially available, and the examples include SY-Glysters MS-310, TS-310, MO-310, PO-310, MS-500, PS-500, MO-500 and PO-500 (Sakamoto Yakuhin Kogyo Co., Ltd.), Sunsofts Q-18F, Q-17F, A-181C, A-171 C, A181E, A171E, A-183E and A-173E (Taiyo Kagaku Co., Ltd.) and Poem J-4581 (Riken Vitamin Co., Ltd.), etc.

The purity of the polyglycerol fatty acid ester is not particularly limited, and it may include two or more ester considering the production thereof.

Further, the surfactants such as components (B) and (C) are not necessarily required as highly purified by distillation, but may be a reaction mixture.

In the water-soluble composition of the present invention, it is preferable that a mixing ratio of/(weight ratio) is 1/(5-0.7), and that a mixing ratio of (weight ratio) is 1/(0.2-1) in order to prepare a stable water-soluble composition.

Component (D)

The component (D), i.e. water, is not particularly limited as far as water is capable of blending to medicines, foods and beverages, cosmetics or feeds; and examples include ion-exchange water, purified water such as distilled water or so, tap water, natural water, alkali ion water. Further, water used therein may contain food additives. Examples of the additives include vitamins, surfactants, stabilizers, seasonings, acids and salts.

Component (E)

Examples of the solubilizer as component (E) include gums, glycitol, saccharides and so on having function of stabilizing solubilized state of coenzyme $Q_{10}$. Specific examples include gums such as gum arabic, xanthan gum, tragacanth gum, guar gum, gellan gum, locustbean gum; polyalcohol such as ethylene glycol, propylene glycol, glycerin, erythritol and so on; monosaccharide and disaccharide such as multitol, restored starch syrup, Lactitol, Palatinit, sorbitol, mannitol, glucose-fructose liquid sugar and milk sugar; and polysaccharides such as dextrin. These solubilizers may be used alone or in combination of two or more kinds thereof. Preferably the solubilizer are reducing saccharides such as glucose-fructose liquid sugar due to sweetness, and gums such as arabia gum due to flavor.

A blending amount of the solubilizer is within the range of 10-80% by weight, preferably 10-70% by weight, and more preferably 15-60% by weight. When the amount of the solubilizer exceeds 80% by weight, the blending content of coenzyme $Q_{10}$ or the surfactants decreases resulting in undesirable difficulty of providing the effect of coenzyme $Q_{10}$ and preparing stable water-soluble composition.

In the invention, one or more other surfactant may be used in combination as far as it does not obstruct the effect of the invention, in addition to (B) polyglycerol fatty acid monoester and (C) polyglycerol fatty acid mono-, di-, tri- or penta-ester. Examples of the surfactants include polyglycerol fatty acid ester other than components (B) and (C), organic acid monoglyceride, glycerin fatty acid ester, sucrose fatty acid ester, sorbitan fatty acid ester, polyoxyethylene sorbitan fatty acid ester (polysorbate), propylene glycol fatty acid ester, lecithin, enzymatic hydrolysis lecithin, saponin, sterol, cholic acid, deoxycholic acid, yucca extract, cationic surfactant, anionic surfactant, ampholytic surfactant, nonionic surfactants other than the above.

A process for producing the water-soluble composition of the present invention will be explained below.

The invention relates to a process for producing the water-soluble composition which comprises the following steps of (I), (II), (III) and/or (IV).

Step (I):

Weighing defined amounts of the components (B), (C), (D) and optionally component (E) respectively, heating and dissolving. For example, it is preferable to heat and dissolve with agitating using three-one-motor or so in a water bath at 60-80° C.

Step (II):

Adding component (A), i.e., coenzyme $Q_{10}$, and mixing.

Step (III):

Homogenizing with the shear force of at least 750 m/minute expressed as a peripheral-speed of an agitation blade using a homo-mixer.

Step (IV):

Homogenizing and under a pressure of at least 98 MPa (1,000 kg/cm$^2$) using homogeneizer.

By the above steps, the average particle diameter of coenzyme $Q_{10}$ which is oil-in-water type emulsion in the composition of the invention become 110 nm or smaller, preferably 80 nm or smaller, and more preferably 60 nm or smaller.

When the average particle diameter exceeds 110 nm, storage stability of the composition, the bioabsorbency and transparency are not sufficient, and the effect of the invention may be not achieved.

Moreover, the average particle diameter is desirably 60 nm or smaller in order to improve the bioabsorbency of coenzyme $Q_{10}$.

Examples of the homo-mixer used in the homogenization treatment of the step (III) include T.K. HOMO MIXER (TOKUSHU KIKA KOGYO Co., Ltd.), Clear MIX (M Technique Co., Ltd.). Applying high shear force agitating with the agitating blade at a peripheral-speed of 750 m/minute or greater, preferably 1000 m/minute or greater, and more preferably 1500 m/minute or greater represents the homogenization method.

Examples of the high pressure homogenizer used for the homogenization of the step (IV) include Microfluidizer (MIZUHO Industrial Co., Ltd.), Ultimaizer (Sugino Machine Limited), etc. The high shear force of 98 MPa (1,000 kg/cm$^2$)

or greater, preferably 150 MPa (1531 kg/cm$^2$) or greater, more preferably 200 MPa (2039 kg/cm$^2$) or greater is employed for the homogenization in the step (IV).

Repeating the homogenization of the step (III) or (IV) alone or performing the steps (III) and (IV) successively enables to provide a homogeneous liquid water-soluble composition containing coenzyme $Q_{10}$. This homogenization procedure preferably conduct twice or more in order to provide a more fine and stable water-soluble composition of coenzyme $Q_{10}$.

Further, various homogenizers such as Nanomizer, ultrasonic emulsifier and various homo-mixers such as AGI HOMO MIXER, Ultra Mixer or so are also employable for the homogenization.

The process for producing the water-soluble composition of the invention, may comprise a natural emulsification method, phase inversion emulsification method, liquid crystal emulsification method, gel emulsification method, D phase emulsification method or PIT emulsification method may be applicable. Moreover, the process of the invention may conduct these methods in combination with mechanical emulsification method such as the foregoing homogenization, etc.

Optionally, oil, lipid, and other oily components that are employable for foods may be blended because coenzyme $Q_{10}$ is an oily component. Examples of the oil employable for foods, include oils made from animals, plants and microorganisms or synthesized oils. Specific examples include lard, beef tallow, chicken oil, whale oil, fish oil, liver oil, soybean oil, cotton seed oil, safflower oil, rice oil, corn oil, rape seed oil, palm oil, beefsteak plant oil, *Perilla ocimoides* oil, cacao butter, peanut oil, coconut oil, evening primrose oil, Borage Oil, milk fat, butter and the oil made by blending synthesized triglyceride such as medium chain triglyceride or so.

Examples of the lipid include specific gravity moderators such as glycosylceramide, Octacosanol, phosphatidylcholine, phosphatidylethanolamine, phosphatidylserine, phosphatidylinositol, phytosterol, lycopene, beta-carotene, lutein, SAIB (sucrose acetic acid/isobutyric acid ester), etc.

Examples of other oily component include fat-soluble vitamins, oil-soluble flavor, hydrocarbons, etc. Specific examples of the fat-soluble vitamin include vitamin A, vitamin D, vitamin E, vitamin K, vitamin P, etc. Specific examples of the oil-soluble flavor include menthol, orange oil, lemon oil, *Citrus junos* oil, essential oil, etc.

Examples of the hydrocarbons include squalene, squalane, lanolin, liquid paraffin, etc.

In the invention, the amount of the oil, lipid and other oily components are not particularly limited because these do not affect use of coenzyme $Q_{10}$, but preferably 0.1-20% by weight.

Although the water-soluble composition containing coenzyme $Q_{10}$ of the present invention may be just used as oil-in-water type emulsion, for example, it may be used as dry powder after removing moisture by spray-drying, etc. Where the dry powder is added into aqueous liquid such as water, the powder may immediately dissolve to give an aqueous solution containing coenzyme $Q_{10}$. Where the powder is taken or consume, it will dissolve into water in the subject and resultantly form an aqueous solution.

The water-soluble composition of the present invention may be just consume, it can be employed as a blending material for adding coenzyme $Q_{10}$ in various kinds of food. Its application is not particularly limited, and it may be applicable to any kind of foods and beverages.

Examples of the foods containing the composition of the invention include beverages such as refreshing drinks, sports beverage, carbonated drinks, health drinks etc; noodles such as udon, spaghetti etc; breads or sweets such as vegetable pancake, bread, cookie, candy, jelly etc; milk flesh processed food such as yogurt, Ham etc; seasoning such as Miso, sauce, liquid soup, mixed sauce, dressing oil etc; processed food such as Tofu, noodles etc; oil processed food such as margarine, low-fat margarine, shortening etc. The examples further include, in consideration of its form, powder food such as powder beverage, powder soup etc; health food product in the shape of capsule, tablet, powder, granule etc; other medicines, medical food, animal feed that are administered as enrichment of nutrient.

Typical examples of the beverage include beverage comprising at least one selected from saline or minerals such as table salt or iron, sourness, sweetener, alcohol, vitamin, flavor, and nectar; namely, refreshing drinks, sports beverage, juice, sour milk beverage, liquor, vitamin mineral beverage, health drink, etc. They further include processed milk, soybean milk, beverage for use in improvement of human's constitution, beverage made by blending with a natural material which can expect physiology effect, thereof.

A convenience of intake prefers beverages such as refreshing drinks, health drinks, etc. These beverages are easily drunk anywhere, surely replenished to those weak senior citizens, dysphagia persons, alimentation of postoperatives and so on who have difficulty in consuming solid, further expecting bioavailability improvement.

In the above application, the amount of coenzyme $Q_{10}$ is not particularly limited, but preferably 0.001-80% by weight in the product.

Examples of cosmetics containing the water-soluble composition of the invention include O/W type lotion, O/W type cream, viscous microemulsion essence, O/W type essence, etc. Various additives usually employable in the technical fields, for example, anti-oxidant, ultraviolet radiation blocking agent, horny cell layer remover, surfactant, odorant, pigment, antiseptic, pH moderator, chelating agent and so on are appropriately blended into the cosmetics of the invention. The cosmetics of the invention are employable in prevention from aging of skin, in prevention and amelioration of rough, dry skin.

This invention will be illustrated with reference to Examples, but not limited thereto.

EXAMPLES

The measuring method and the evaluation method used will be illustrated below.

1. Measuring Method of an Average Particle Diameter

The average particle diameter of samples was determined by measuring dispersed particle using a submicron particle size distribution measuring apparatus [Type N4SD; Beckman Coulter, Inc.].

2. Acid Resistance & Heat Resistance Test

A water-soluble composition comprising coenzyme $Q_{10}$ was added in an amount of 1% by weight into purified water at pH 3 or less adjusted with citric acid, and the acid aqueous solution containing the water-soluble composition was incubated in a water bath for 30 minutes, from the time when the temperature reached to 85° C. The acid solution was cooled to room temperature and the acid resistant & heat resistant property was evaluated by its average particle diameter after 1 day.

3. Salt-Resistance & Heat Resistance Test

A water-soluble composition comprising coenzyme $Q_{10}$ was added in an amount of 1% by weight to purified water containing table salt of 5% by weight, and the salt solution was incubated for 30 min. in a water bath from the time when the temperature reached to 85° C., the salt solution was heat-treated for 30 minutes. The solution was cooled to room temperature and the salt-resistance & and heat resistance was evaluated by its average particle diameter after 1 day.

Example 1

Decaglycerinmonooleate of 12% by weight, pentaglycerintrioleate of 5% by weight and water 78% by weight were warmed and dissolved completely to form an aqueous phase. Coenzyme $Q_{10}$ (Food material coenzyme $Q_{10}$, Nissin Pharma Inc.) of 5% by weight was gently added to the aqueous phase with stirring and subsequently the mixed solution was homogenized under 150 MPa (1531 kg/cm$^2$) with a high pressure homogenizer, thereby resultantly preparing uniform water-soluble composition. The composition was evaluated by the foregoing methods.

Constitution of the composition and results of the evaluation are shown in Table 1. In Table 1, "AA" means that uniformity is within ±10 nm where the particle diameter is smaller than 100 nm; and uniformity is within ±10% where the particle diameter is 100 nm or greater; exhibiting favorable stability. "BB" means that uniformity is within ±20 nm where the particle diameter is smaller than 100 nm and uniformity is within ±20% where the particle diameter is 100 nm or greater, exhibiting slightly poor stability. "CC" means that the stability is poor and reveals fluctuation outside of the above range.

Example 2

Decaglycerinmonooleate of 9.5% by weight, pentaglycerinmonooleate of 6.5% by weight, water of 24% by weight and glucose-fructose liquid sugar of 50% by weight were warmed and dissolved completely to form an aqueous phase. Coenzyme $Q_{10}$ of 10% by weight was gently added to the aqueous phase with stirring and subsequently the mixed solution was processed at 1500 m/minute of a blade peripheral speed for 15 min. with a homo-mixer, then, homogenized under 200 MPa (2039 kg/cm$^2$) with a high pressure homogenizer, thereby resultantly preparing uniform water-soluble composition. The composition was evaluated in the same manner as Example 1. Constitution of the composition and results of evaluation are shown in Table 1.

Example 3

Decaglycerinmonooleate of 9.5% by weight, pentaglycerinmonooleate of 6.5% by weight, water of 18% by weight and glucose-fructose liquid sugar of 52% by weight were warmed and dissolved completely to form an aqueous phase. Coenzyme $Q_{10}$ of 10% by weight and palm oil of 4% by weight preparedly mixed and dissolved as oil phase were gently added to the aqueous phase with stirring and subsequently the mixed solution was processed at 1500 m/minute of the blade peripheral speed for 15 minutes with a homo-mixer, then, homogenized under 200 MPa (2039 kg/cm$^2$) with a high pressure homogenizer, thereby resultantly preparing uniform water-soluble composition. The composition was evaluated in the same manner as Example 1. Constitution of the composition and results of the evaluation are shown in Table 1.

Example 4

Decaglycerinmonooleate of 9.5% by weight, pentaglycerinmonooleate of 4% by weight, citric acid monoglyceride of 2% by weight, water of 55.5% by weight and Gum Arabic of 19% by weight were warmed and dissolved completely to form an aqueous phase. Coenzyme $Q_{10}$ of 10% by weight was gently added to the aqueous phase with stirring and subsequently the mixed solution was processed at 1800 m/minute of a blade peripheral speed for 60 min. with a homo-mixer, thereby resultantly preparing homogeneous water-soluble composition. The composition was evaluated in the same manner as Example 1. Constitution of the composition and results of the evaluation are shown in Table 1.

Example 5

Decaglycerinmonooleate of 13.5% by weight, hexaglycerinmonooleate of 6.5% by weight, water of 31% by weight and reducing starch sugar of 30% by weight warmed and dissolved completely to form an aqueous phase. Coenzyme $Q_{10}$ of 15% by weight and SAIB of 4% by weight preparedly mixed and dissolved as an oil phase were gently added to the aqueous phase with stirring and subsequently the mixed solution was processed at 1500 m/minute of a blade peripheral speed for 15 minutes with a homo mixer, then, homogenized under 245 MPa (2500 kg/cm$^2$) with a high pressure homogenizer, thereby resultantly preparing uniform water-soluble composition. The composition was evaluated in the same manner as Example 1. Constitution of the composition and results of the evaluation are shown in Table 1.

Example 6

Decaglycerinmonooleate of 13.5% by weight, tetraglycerinmonooleate of 6.5% by weight, water of 31% by weight and reducing starch sugar of 30% by weight warmed and dissolved completely to form an aqueous phase. Coenzyme $Q_{10}$ of 15% by weight and SAIB of 4% by weight preparedly mixed and dissolved were gently added to the aqueous phase with stirring and subsequently the mixed solution was processed at 1500 m/minute of a blade peripheral speed for 20 minutes with a homo mixer, then, homogenized under 245 MPa (2500 kg/cm$^2$) with a high pressure homogenizer, thereby resultantly preparing uniform water-soluble composition. The composition was evaluated in the same manner as Example 1. Constitution of the composition and results of the evaluation are shown in Table 1.

Example 7

Decaglycerinmonooleate of 12.5% by weight, pentaglycerinmonooleate of 8.5% by weight, water of 19% by weight and glucose-fructose liquid sugar of 30% by weight were warmed and dissolved completely to form an aqueous phase. Coenzyme $Q_{10}$ of 30% by weight was gently added to the aqueous phase with stirring and subsequently the mixed solution was homogenized under 150 MPa (1531 kg/cm$^2$) with a high pressure homogenizer, then, homogenized under 200 MPa (2039 kg/cm$^2$) with the homogenizer twice, thereby resultantly preparing uniform composition. The composition was evaluated in the same manner as Example 1. Constitution of the composition and results of the evaluation are shown in Table 1.

Comparative Example 1

Comparative Example 1 was performed similarly as Example 1 except that were replaced by decaglycerinmonooleate of 17% by weight was used in stead of decaglycerinmonooleate of 12% by weight and pentaglycerinmonooleate of 5% by weight thereby resultantly preparing uniform composition. The composition was evaluated in the same manner as Example 1. Constitution of the composition and results of the evaluation are shown in Table 1.

Comparative Example 2

Comparative Example 2 was performed similarly as Example 1 except that were replaced by decaglycerinmonostearate of 17% by weight was used in stead of decaglycerinmonooleate of 12% by weight and pentaglycerinmonooleate of 5% by weight thereby resultantly preparing uniform composition. The composition was evaluated in the same manner as Example 1. Constitution of the composition and results of the evaluation are shown in Table 1.

Comparative Example 4

Decaglycerinmonooleate of 40% by weight, pentaglycerinmonoolete of 20% by weight and water of 30% by weight were warmed and dissolved completely to form an aqueous phase. Coenzyme $Q_{10}$ of 10% by weight was gently added to the aqueous phase with stirring and subsequently the mixed solution was processed at 1500 m/of a blade peripheral speed for 15 minutes with a homo-mixer, then, homogenized under 200 MPa (2039 kg/cm$^2$) with a high pressure homogenizer, however, failed in forming any water-soluble composition because the viscosity of the resultant composition was considerably high.

In Tables, "Ex.", "Co. Ex.", "B. C." and "R." means "Example", "Comparative Example", "Blending Cnsituents" and "Results" each as their abbreviation respectively.

TABLE 1

Constitution (%) of water-soluble composition and Results

| | | | Ex. 1 | Ex. 2 | Ex. 3 | Ex. 4 | Ex. 5 | Ex. 6 | Ex. 7 | Co. Ex. 1 | Co. Ex. 2 | Co. Ex. 3 | Co. Ex. 4 |
|---|---|---|---|---|---|---|---|---|---|---|---|---|---|
| B. C | A | Coenzyme $Q_{10}$ | 5 | 10 | 10 | 10 | 15 | 15 | 30 | 5 | 5 | 10 | 10 |
| | B | Decaglycerinmonooleate | 12 | 9.5 | 9.5 | 9.5 | 13.5 | 13.5 | 12.5 | 17 | | 3 | 40 |
| | C | Pentaglycerintrioleate | 5 | | | | | | | | | | |
| | C | Pentaglycerinmonooleate | | 6.5 | 6.5 | 4 | | | 8.5 | | | 0.5 | 20 |
| | C | Hexaglycerinmonooleate | | | | | 6.5 | | | | | | |
| | C | Tetraglycerinmonooleate | | | | | | 6.5 | | | | | |
| | Others | Citric acid monoglyceride | | | | 2 | | | | | | | |
| | Others | Decaglycerinmonostearate | | | | | | | | | 17 | | |
| | D | Water | 78 | 24 | 18 | 55.5 | 31 | 31 | 19 | 78 | 78 | 34.5 | 30 |
| | E | Glucose-fructose liquid sugar | | 50 | 52 | | | | 30 | | | 52 | |
| | E | Gum Arabic | | | | 19 | | | | | | | |
| | E | Reducing starch sugar | | | | | 30 | 30 | | | | | |
| | Others | Palm Oil | | | | 4 | | | | | | | |
| | Others | Specific gravity moderator | | | | | 4 | 4 | | | | | |
| | | Sum | 100 | 100 | 100 | 100 | 100 | 100 | 100 | 100 | 100 | 100 | 100 |
| | | A/(B + C) | 1/3.4 | 1/1.6 | 1/1.6 | 1/1.6 | 1/1.3 | 1/1.3 | 1/0.7 | 1/3.4 | 1/3.4 | 1/0.4 | 1/6 |
| | | B/C | 1/0.4 | 1/0.7 | 1/0.7 | 1/0.4 | 1/0.5 | 1/0.5 | 1/0.7 | — | — | 1/0.2 | 1/0.5 |
| R. | | Particle Diameter (nm) | 108.0 | 49.5 | 48.2 | 76.5 | 58.3 | 68.0 | 88.0 | 107.0 | 126.0 | 473.0 | Disabled* |
| | | Acid resistance | 103.0 | 49.3 | 49.5 | 75.8 | 57.2 | 63.7 | 86.0 | 112.0 | 120.0 | 488.0 | — |
| | | Acid resistance & heat resistance | 101.0 | 50.9 | 58.2 | 76.0 | 60.2 | 63.0 | 95.9 | 120.0 | 134.0 | Separation | — |
| | | Evaluation results | AA | AA | AA | AA | AA | AA | AA | BB | BB | CC | — |
| | | Salt-resistance | 101.0 | 49.7 | 49.1 | 75.5 | 58.5 | 64.1 | 85.0 | 109.0 | 122.0 | 483.0 | — |
| | | Salt-resistance & heat resistance | 102.0 | 51.1 | 58.0 | 77.5 | 62.7 | 70.6 | 97.2 | 135.0 | 138.0 | Separation | — |
| | | Evaluation results | AA | AA | AA | AA | AA | AA | AA | CC | BB | CC | — |

*Preparation disabled because of over viscosity

Comparative Example 3

Decaglycerimonooleate 3% by weight, pentaglycerinmonoolete of 0.5% by weight, water of 34.5% by weight and glucose-fructose liquid sugar of 52% by weight were warmed and dissolved completely to form an aqueous phase. Coenzyme $Q_{10}$ of 10% by weight was added to the aqueous phase with stirring and subsequently the mixed solution was processed at 1500 m/minute of a blade peripheral speed for 15 minutes with a homo-mixer, then, homogenized under 200 MPa (2039 kg/cm$^2$) with a high pressure homogenizer, thereby resultantly preparing uniform composition. The composition was evaluated in the same manner as Example 1.

The above results revealed that compositions of Comparative Example 1 wherein the solubilizer was decaglycerinmonooleate only and Comparative Example 2 wherein the particle diameter was 110 nm or greater are inferior in acid resistant & heat resistant properties and in salt-resistant & heat resistant properties.

The composition of Comparative Example 3 wherein the amounts of (B) decaglycerinmonooleate and (C) pentaglycerinmonooleate were less than the range defined in the invention has large particle diameter of the composition and is inferior in acid resistant & heat resistant properties and salt-resistant & heat resistant properties.

In Comparative Example 4 wherein the amounts of (B) decaglycerinmonooleate and (C) pentaglycerinmonooleate were greater than the range defined in the invention, it was impossible to prepare any stable water-soluble composition.

On the contrary, it is apparently verified that Examples 1-7 according to the invention succeeded in preparing the water-soluble composition with the particle diameter of 110 nm or smaller, good stably and superior in acid resistant & heat resistant properties and salt-resistant & heat resistant properties.

Example 8

Decaglycerinmonostearate of 16% by weight, pentaglycerinmonostearate of 4% by weight, water of 20% by weight and glucose-fructose liquid sugar of 50% by weight were warmed and dissolved completely to form an aqueous phase. Coenzyme $Q_{10}$ as an oil phase of 10% by weight was gently added to the aqueous phase with stirring and subsequently the mixed solution was processed treated at 1500 m/minute of a blade peripheral speed for 15 minutes with a homo-mixer, then, homogenized under 200 MPa (2039 kg/cm$^2$) with a high pressure homogenizer, thereby resultantly preparing uniform composition.

The composition was evaluated in the same manner as Example 1. Constitution of the composition and results of the evaluation are shown in Table 2.

Example 9

Decaglycerinmonooleate of 16% by weight, pentaglycerinmonostearate of 4% by weight, water of 20% by weight and glucose-fructose liquid sugar of 50% by weight were warmed and dissolved completely to form an aqueous phase. Coenzyme $Q_{10}$ of 10% by weight was gently added to the aqueous phase with stirring and subsequently the mixed solution was processed at 1500 m/minute for 15 minute with a homo-mixers, then, homogenized under 200 MPa (2039 kg/cm$^2$) with a high pressure homogenizer, thereby resultantly preparing uniform composition. The composition was evaluated in the same manner as Example 1. Constitution of the composition and results of the evaluation are shown in Table 2.

Example 10

Decaglycerinmonostearate of 8% by weight, decaglycerinmonolinoleate of 8% by weight, pentaglycerinmonostearate of 4% by weight, water of 20% by weight and glucose-fructose liquid sugar of 46% by weight were warmed and dissolved completely to form an aqueous phase. Coenzyme $Q_{10}$ of 10% by weight and palm oil of 4% by weight preparedly mixed and dissolved as an oil phase were gently added to the aqueous phase with stirring and subsequently the mixed solution was processed at 1500 m/minute of a blade peripheral speed for 15 minutes with a homo-mixer, then, homogenized under 200 MPa (2039 kg/cm$^2$) with a high pressure homogenizer, thereby resultantly preparing uniform composition. The composition was evaluated in the same manner as Example 1. Constitution of the composition and results of the evaluation are shown in Table 2.

Example 11

Decaglycerinmonooleate of 8% by weight, decaglycerinmonolinoleate of 8% by weight, pentaglycerinmonooleate of 4% by weight, water of 20% by weight and glucose-fructose liquid sugar of 46% by weight were warmed and dissolved completely to form an aqueous phase. Coenzyme $Q_{10}$ as an oil phase of 10% by weight was gently added to the aqueous phase with stirring and subsequently the mixed solution was processed at 1500 m/minute of a blade peripheral speed for 15 minutes with a homo-mixer, then, homogenized under 200 MPa (2039 kg/cm$^2$) with a high pressure homogenizer, thereby resultantly preparing uniform composition. The composition was evaluated in the same manner as Example 1. Constitution of the composition and results of the evaluation are shown in Table 2.

TABLE 2

| | | | Ex. 8 | Ex. 9 | Ex. 10 | Ex. 11 |
|---|---|---|---|---|---|---|
| | Composition (%) of water-soluble composition | | | | | |
| B.C. | A | Coenzyme Q10 | 10 | 10 | 10 | 10 |
| | B | Decaglycerin monostearate | 16 | | 8 | |
| | B | Decaglycerin monooleate | | 16 | | 8 |
| | B | Decaglycerin monolinoleate | | | 8 | 8 |
| | C | Pentaglycerin monostearate | 4 | 4 | 4 | |
| | C | Pentaglycerin monooleate | | | | 4 |
| | D | Water | 20 | 20 | 20 | 20 |
| | E | Glucose-fructose Liquid sugar | 50 | 50 | 46 | 50 |
| | Others | Palm Oil | | | 4 | |
| | | Sum | 100 | 100 | 100 | 100 |
| | | A/(B + C) | 1/2 | 1/2 | 1/2 | 1/2 |
| | | B/C | 1/0.25 | 1/0.25 | 1/0.25 | 1/0.25 |
| R. | | Particle Diameter (nm) | 69.2 | 59.6 | 80.6 | 78.3 |
| | | Acid resistance | 66.1 | 62.5 | 89.3 | 81.3 |
| | | Acid resistance & heat resistance | 67.1 | 62.6 | 88.4 | 79.9 |
| | | Evaluation | AA | AA | AA | AA |
| | | Salt-resistance | 66.7 | 60.3 | 88.6 | 78.4 |
| | | Salt-resistance & heat resistance | 65.5 | 62.8 | 86.7 | 81.1 |
| | | Evaluation | AA | AA | AA | AA |

As the results, it is verified that Examples 8 to 11 wherein at least one oleic acid ester in Component (B) or (C) was substituted with the other fatty acid ester having 18 carbon atoms or its mixture also succeeded in preparing the water-soluble composition having the particle diameter of 110 nm or smaller, good stably and superior in acid resistant & heat resistant properties and salt-resistant & heat resistant properties.

Example 12

A beverage consisting of the water-soluble composition of Example 2 or Example 3 of 0.3% by weight, glucose-fructose liquid sugar of 15% by weight, granulated sugar of 7% by weight, 5 times concentrated grapefruit juice of 4% by weight, citric acid of 0.3% by weight, sodium citrate of 0.2% by weight, grapefruit flavor of 0.2% by weight and water of 73% by weight it was prepared, filled into a 100 ml bottle and then, sterilized at 85° C. for 30 minutes.

De-emulsion of coenzyme $Q_{10}$ was not recognized after the sterilization and the beverage was drinkable without any problem.

Comparative Example 5

Tetraglycerinmonostearate of 9 parts by weight, decaglycerinmonostearate of 6 parts by weight, glycerin of 5 parts by weight and water of 70 parts by weight were warmed and dissolved completely to form an aqueous phase. Coenzyme $Q_{10}$ of 10 parts by weight was gently added to the aqueous phase with stirring and subsequently the mixed solution was processed for 5 minutes with a homo-mixer, thereby resultantly preparing a dispersed solution of coenzyme $Q_{10}$ having average particle diameter of 380 nm. The emulsified state just after the preparation was good, however, de-emulsion was found in the upper part 2 weeks later.

Comparative Example 6

Emulsified Powders

Coenzyme $Q_{10}$ of 100 g was melted by warming and added into 200 g of glucose fatty acid ester preparedly melted by warming at 60° C. and they were further emulsified. After passing them through high pressure homogenizer (H-11; SANWA MACHINE CO., INC.), they were atomized during flowing excipient mixture consisting of milk sugar of 1000 g and starch of 700 g with a fluidized-bed type granulator (FLO-MINI; Freund Corporation) to form orange colored powdery or granular composition. Throwing 1 g of the powder composition into 100 g of water immediately dispersed and dissolved to give pale yellowish dispersion comprising coenzyme $Q_{10}$. By measuring the particle diameter of the dispersed coenzyme $Q_{10}$ in the dispersion, a 50% particle diameter was 2.62 μm.

Comparative Example

Soft Capsule

Coenzyme $Q_{10}$ of 60 g, soybean oil of 240 g and glycerin fatty acid ester (COCONARD MT) of 300 g were warmed and dissolved at 60° C. After assuring the dissolution of coenzyme $Q_{10}$, the mixed solution was cooled to around 25° C., thereby preparing capsule filling fluid. Subsequently, soft capsules each containing 30 mg of coenzyme $Q_{10}$ were prepared using the conventional technique.

Reference Test 1

The water-soluble compositions of Example 2 and Comparative Example 5 were compared with respect to absorbency of coenzyme $Q_{10}$ by animal test.

<Absorption Test on Animals>

Two groups of 3 beagle dogs (males) per group were employed for the absorption test. Fasting from after 17:00 in the day before administration, hard capsules containing the composition of Example 2 and the dispersion of Comparative Example 5 with coenzyme $Q_{10}$ 90 mg/dog of dosage respectively were forcedly administrated to all the dogs once. Sampling blood regularly until 24 hours after the administration, the concentration of coenzyme $Q_{10}$ in plasma were determined. The results are shown in Table 3.

<Method for Measuring Coenzyme $Q_{10}$ in Plasma>

The measurement of coenzyme $Q_{10}$ in plasma was carried out using High Performance Liquid Chromatography (HPLC) under the following conditions. Additionally, because there are both oxidized and reduced types of coenzyme $Q_{10}$ in plasma, the samples were subjected to the measurement by HPLC after converting reduced type to oxidation type by adding iron oxide.

<HPLC Condition>
Column: Nucleosil 5C18, 4.6 mm φ×25 cm,
Moving phase: Ethanol/Acetonitrile (=60/40 volume ratio),
Flow rate: 1 ml/minute,
Detector: UV spectroscopy photometer,
Detecting wave length=275 nm.

TABLE 3

| Sample (Particle Diameter) | Reference Test | |
|---|---|---|
| | Ex. 2 49.5 nm | Co. Ex. 6 380 nm |
| Cmax (μg/ml) | 1.172 ± 1.72 | 0.583 ± 2.01 |
| tmax (hr) | 5.88 ± 0.9 | 6.24 ± 1.2 |
| AUC (0→t) (μg · hr/ml) | 11.2 ± 0.67 | 6.31 ± 0.88 |

Cf. Cmax (μg/ml): Maximum concentration in blood
tmax (hr): Time until maximum concentration in blood AUC (0→24) (μg·hr/ml): Area under curve of drug concentration in blood/time.

As the results, it is verified that bioabsorbency was significantly high in the case where the water-soluble composition of Example 2 having smaller particle diameters was administered, in comparison with the dispersion of Comparative Example 5. Absorbency of coenzyme $Q_{10}$ during fasting was usually considered poor, however, it is confirmed that the administration of the water-soluble composition containing coenzyme $Q_{10}$ having small particle diameters of the invention may conspicuously improve its bioabsorbency.

Reference Test 2; Absorbency Test During Fasting

The absorbency test during fasting was carried out by oral administration of the water-soluble composition of Example 2, the emulsified powder composition of Comparative Example 6 or the soft capsule of Comparative Example 7 each to three subjects respectively.

Fasting from after 21:00 on day before the administration, coenzyme $Q_{10}$ 60 mg was orally administered to the subjects at 8:00 on next morning under fasting. Sampling blood 2, 4, 6, 8, 12 and 24 hours after the administration, the concentration of coenzyme $Q_{10}$ in blood were measured. The measurement of the concentration was carried out using HPLC under the following conditions. Because there are both oxidied and reduced types of coenzyme $Q_{10}$ in blood, the concentration were determined by adding the measured values of both types.

Column: Nhdeosil 5C18 4.6 mm×25 cm
Moving phase: ethanol: acetonitrile (55:45):
Flow rate: 1 ml/minute
Detector: UV spectroscopy photometer 275 nm Results show that both the emulsified powder composition of Comparative Example 6 and the soft capsule of Comparative Example 7 gave extremely little rise of the concentration in blood after the administration and were almost not absorbed. However, it is confirmed that the water-soluble composition of Example 2 may give bioabsorption of coenzyme $Q_{10}$ surely with high level even by the administration under fasting. Although the previous knowledge teaches that absorption of coenzyme $Q_{10}$ was not achieved unless consuming together with eating, it is confirmed that the water-soluble composition according to the invention may conspicuously improve the absorbency even under fasting. These results are shown in FIG. 1.

Reference Test 3; Absorbency Test After Eating

The absorbency test after eating was carried out by oral administration of the composition of Example 2, the emulsified powder composition of Comparative Example 6 and the soft capsule of Comparative Example 7 each to three subjects respectively.

After finishing a meal until 22:00 on day before the administration, blood was sampled from each subject respectively in the next morning, and then, 60 mg of coenzyme $Q_{10}$ was orally administered to the subjects within 10 minutes after the breakfast. Sampling blood 2, 4, 6, 8, 12 and 24 hours after the administration, the concentrations of coenzyme $Q_{10}$ in blood were measured in the same manner as Reference Test 2.

Figure 2:
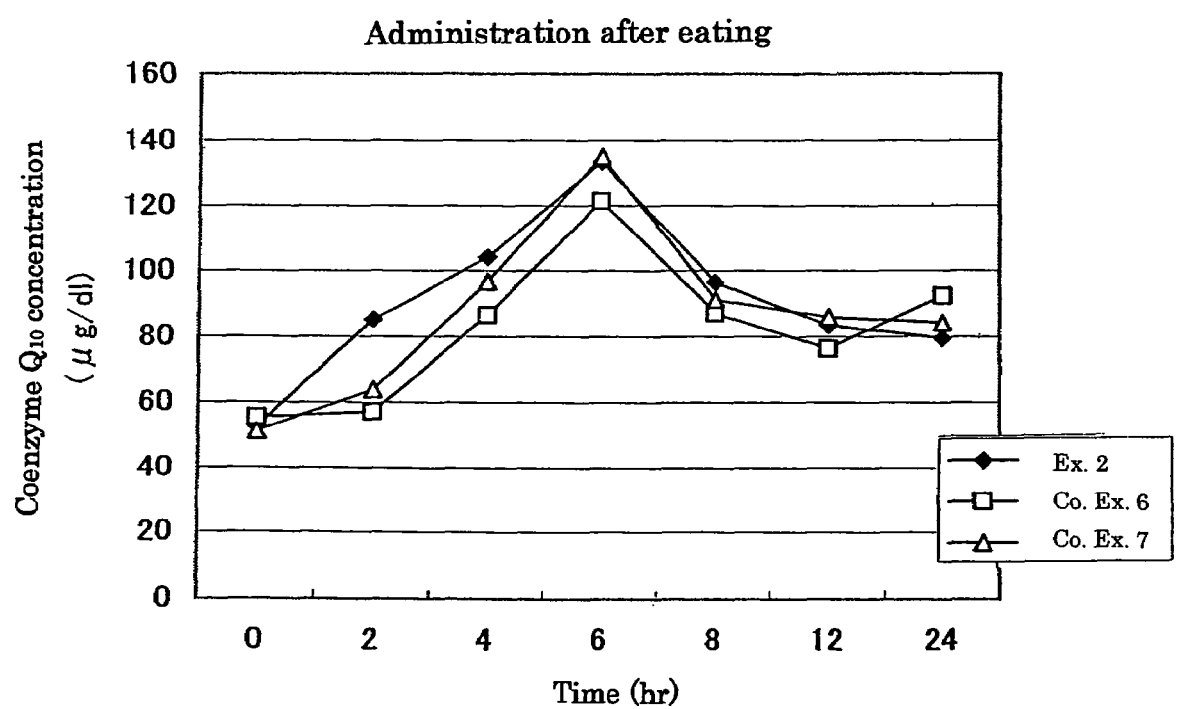
FIG. 2 is a graph which illustrating the absorbency of coenzyme $Q_{10}$ in after-meal intake.

Results show that both the emulsified powder composition of Comparative Example 6 and the soft capsule of Comparative Example 7 initiated elevation of the concentration two hours after the administration, the composition of Example 2 initiated elevation immediately after the administration and exhibited extremely faster rise of the increase in the absorbed amount than the comparative examples. It is confirmed that the water-soluble composition of the invention was extremely superior in bioabsorbency. These results are shown in FIG. 2.

INDUSTRIAL APPLICABILITY

The water-soluble composition containing coenzyme $Q_{10}$ according to the present invention is superior in storage stability, and is capable of maintaining an uniform and stable state without precipitating coenzyme $Q_{10}$ during a long term storage. The composition of the invention is superior in acid resistance, salt-resistance and heat resistance, and further enables to maintain good water-soluble state even blending to medicines, foods and beverages, cosmetics, feeds, additives usually employed therein. The composition is stable against heating, and acceptable of high-temperature disinfection or sterilization. Furthermore, the composition of the invention is conspicuously improved in absorbency of coenzyme $Q_{10}$ Particularly, sufficient amounts of coenzyme $Q_{10}$ can be consumed even when being hungry.

Although the water-soluble composition of the invention may be directly consumed, blending it to medicines, foods and beverages, cosmetics or feeds may achieve effective adsorption of sufficient amount of coenzyme $Q_{10}$. Particularly, the composition can surely supply coenzyme $Q_{10}$ to those weak senior citizens, dysphagia persons, alimentation of postoperatives who have difficulty swallowing of solid matters.

What is claimed is:

1. A water-soluble composition which comprises (A) coenzyme $Q_{10}$ of 5 to 40% by weight, (B) monoester of polyglycerol with averaged polymerization degree of 10 and fatty acid having 18 carbon atoms of 5 to 30% by weight, (C) mono-, di-, tri- or penta-ester of polyglycerol with average polymerization degree of 3-6 and fatty acid having 18 carbon atoms of 1 to 18% by weight, and (D) water, wherein an averaged particle diameter of the water-soluble composition is 110 nm or smaller.

2. The water-soluble composition of claim 1, wherein said fatty acid composing component (B) is stearic acid, oleic acid or linoleic acid, and wherein said fatty acid composing component (C) is stearic acid, oleic acid or linoleic acid.

3. The water-soluble composition of claim 1, further comprises (E) a solubilizer of 10 to 80% by weight.

4. The water-soluble composition of claim 3, wherein said solubilizer is gum, saccharide or polyhydric alcohol.

5. The water-soluble composition of claim 1, wherein a weight ratio of [(A)]/[(B)+(C)] is within the range of 1/(5 -0.7) and wherein a weight ratio of [(B)]/[(C)] is within the range of 1/(0.2 -1).

6. A process for producing the water-soluble composition according to claim 1 which comprises the steps of:
   (I) heating and dissolving the components (B), (C), and (D);
   (II) adding component (A) and mixing; and at least one selected from
   (III) homogenizing the resultant mixture with a shear force of 750 m/minute or greater as a peripheral-speed of an agitation blade using a homo-mixer; or
   (IV) homogenizing the resultant mixture under a homogenizing pressure of 98 MPa (1,000 kg/cm$^2$) or greater using a homogenizer.

7. The process of claim 6, wherein said step (III) or (IV) is repeated, or wherein the steps (III) and (IV) are successively carried out.

8. Medicines containing said water-soluble composition described in claim 1.

9. Foods and beverages containing said water-soluble composition described in claim 1.

10. Cosmetics containing said water-soluble composition described in claim 1.

11. Feeds containing said water-soluble composition described in claim 1.

12. The water-soluble composition of claim 2, further comprises (E) a solubilizer of 10 to 80% by weight.

13. The water-soluble composition of claim 12, wherein said solubilizer is gum, saccharide or polyhydric alcohol.

14. A water-soluble composition which comprises (A) coenzyme $Q_{10}$ of 5 to 40% by weight, (B) monoester of polyglycerol with averaged polymerization degree of 10 and fatty acid having 18 carbon atoms of 5 to 30% by weight, (C) mono-, di-, tri- or penta-ester of polyglycerol with average polymerization degree of 3-6 and fatty acid having 18 carbon atoms of 1 to 18% by weight, and (D) water, wherein an average particle diameter of the (A) coenzyme $Q_{10}$ in the water-soluble composition is 110 nm or smaller.

15. The water-soluble composition of claim 14, wherein said average particle diameter is 80 nm or smaller.

16. The water-soluble composition of claim 14, wherein said average particle diameter is 60 nm or smaller.

17. A process for producing the water-soluble composition according to claim 3 which comprises the steps of:
   (I) heating and dissolving the components (B), (C), (D) and (E);
   (II) adding component (A) and mixing; and at least one selected from
   (III) homogenizing the resultant mixture with a shear force of 750 m/minute or greater as a peripheral-speed of an agitation blade using a homo-mixer; or
   (IV) homogenizing the resultant mixture under a homogenizing pressure of 98 MPa (1,000 kg/cm$^2$) or greater using a homogenizer.

18. The process of claim 17, wherein said step (III) or (IV) is repeated, or wherein the steps (III) and (IV) are successively carried out.

* * * * *